(12) United States Patent
Gonzalez-Garcia et al.

(10) Patent No.: US 8,993,568 B2
(45) Date of Patent: Mar. 31, 2015

(54) MORPHOLINYL DERIVATIVES USEFUL AS MOGAT-2 INHIBITORS

(71) Applicant: Eli Lilly and Company, Indianapolis, IN (US)

(72) Inventors: Maria Rosario Gonzalez-Garcia, Madrid (ES); Maria Carmen Fernandez, Madrid (ES)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 14/372,833

(22) PCT Filed: Jan. 24, 2013

(86) PCT No.: PCT/US2013/022828
§ 371 (c)(1),
(2) Date: Jul. 17, 2014

(87) PCT Pub. No.: WO2013/116065
PCT Pub. Date: Aug. 8, 2013

(65) Prior Publication Data
US 2015/0005305 A1 Jan. 1, 2015

Related U.S. Application Data

(60) Provisional application No. 61/617,093, filed on Mar. 29, 2012.

(30) Foreign Application Priority Data

Jan. 31, 2012 (EP) .................... 12382037
Nov. 6, 2012 (EP) .................... 12382433

(51) Int. Cl.
C07D 295/135 (2006.01)
A61K 31/5375 (2006.01)
C07C 57/145 (2006.01)

(52) U.S. Cl.
CPC .......... C07D 295/135 (2013.01); C07C 57/145 (2013.01)
USPC ...................... 514/239.5; 544/162

(58) Field of Classification Search
USPC ............................. 514/239.5, 162
See application file for complete search history.

(56) References Cited

U.S. PATENT DOCUMENTS

| | | | |
|---|---|---|---|
| 5,889,006 A | 3/1999 | Lowe et al. | |
| 6,303,816 B1 | 10/2001 | Arnold et al. | |
| 6,387,954 B1 | 5/2002 | Jones et al. | |
| 6,500,865 B1 | 12/2002 | Arnold et al. | |
| 8,575,352 B2 | 11/2013 | Fernandez et al. | |
| 2009/0163545 A1 | 6/2009 | Goldfarb | |
| 2009/0221577 A1 | 9/2009 | Branch et al. | |
| 2010/0093771 A1 | 4/2010 | Nakamura et al. | |
| 2011/0015198 A1 | 1/2011 | Kamijo et al. | |
| 2011/0275647 A1 | 11/2011 | Arakawa et al. | |

FOREIGN PATENT DOCUMENTS

| | | |
|---|---|---|
| EP | 1655283 | 8/2004 |
| EP | 1659113 | 8/2004 |
| EP | 2078719 | 9/2014 |
| WO | 2009147211 | 12/2009 |
| WO | 2010095767 | 8/2010 |
| WO | 2012091010 | 5/2012 |
| WO | 2013112323 | 8/2013 |
| WO | 2013116065 | 8/2013 |
| WO | 2014074365 | 5/2014 |

OTHER PUBLICATIONS

Yen, et al., "MGAT2, a Monoacylglycerol Acyltransferase Expressed in the Small Intestine," The Journal of Biological Chemistry, vol. 278, No. 20, Issue of May 16, pp. 18532-18537 (2003).
Hall, et al., "Evidence for regulated monoacylglycerol acyltransferase expression and activity in human liver," Journal of Lipid Research, vol. 53, pp. 990-999 (2012).
Cao, et al., "A Predominant Role of Acyl-CoA:monoacylglycerol Acyltransferase-2 in Dietary Fat Absorption Implicated by Tissue Distribution, Subcellular Localization, and Up-regulation by High Fat Diet," The Journal of Biological Chemistry, vol. 279, No. 18, Issue of Apr. 30, pp. 18878-18886 (2004).
Yen, et al., "Deficiency of the intestinal enzyme acyl CoA:monoacylglycerol acyltransferase-2 protects mice from metabolic disorders induced by high-fat feeding," Nature Medicine, vol. 15, No. 4, pp. 442-446 (2009).
Olsson, et al, "Rosuvastatin: A Highly Effective New HMG-CoA Reductase Inhibitor," Cardiovascular Drug Reviews, vol. 20, No. 4, pp. 303-328, (2002).

*Primary Examiner* — Rebecca Anderson
(74) *Attorney, Agent, or Firm* — James B. Myers

(57) ABSTRACT

The present invention provides compounds of Formula I or a pharmaceutical salt thereof, methods of treating hypertriglyceridemia using the compounds; and a process for preparing the compounds.

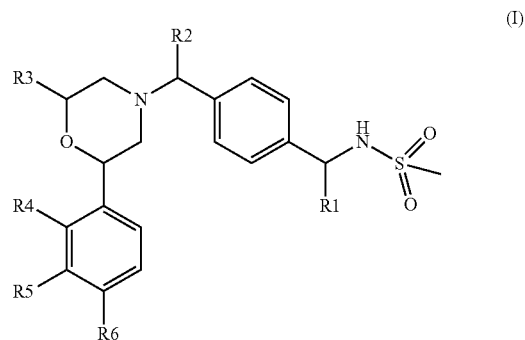

18 Claims, No Drawings

MORPHOLINYL DERIVATIVES USEFUL AS MOGAT-2 INHIBITORS

Ingestion of excess dietary fat is a leading cause of diet induced obesity and can have a profound detrimental effect on a people's health. More than 90% of dietary fat for humans is triacylglycerol (or triglyceride), which is nearly completely absorbed by the small intestine. The enzyme acyl CoA:monoacylglycerol acytransferase-2 (MOGAT-2) is believed to play an important role in the absorption of dietary fat in the small intestines. It has been demonstrated that MOGAT-2 deficient mice when fed a high fat diet are protected against developing obesity, glucose intolerance, hypercholesterolemia and developing a fatty liver. Further, it has also been shown that MOGAT-2 deficient mice exhibit lower plasma triacylglycerol levels after a dietary olive oil challenge. (Yen, et al, *Nat. Med.* 2009, 15(4), 442-446.)

There is a need for additional drugs for the treatments of hypertriglyceridemia. There is also a need to for new inhibitors of the MOGAT-2 receptor. The present invention addresses one or more of these needs by providing alternative compounds and treatment methods, which may be suitable for the treatment hypertriglyceridemia.

The present invention provides a compound of Formula I

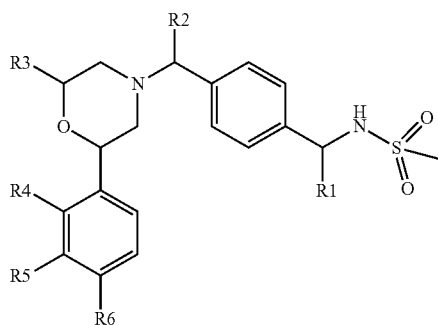

wherein R1 is selected from: —$CH_3$ and —$CF_3$; R2 is selected from: H and —$CH_3$; R3 is selected from: H and —$CH_3$; R4 is selected from: H, —$OC_{1-3}$alkyl, and halogen; R5 is selected from: H, —$CF_3$, —$OCH_3$, and halogen; R6 is selected from: H and halogen; provided that at least one of R4, R5, and R6 is H; or a pharmaceutically acceptable salt thereof. Compounds of the present invention can have one or more chiral centers. In the compounds of Formula II below, one of the chiral centers is identified with an asterisk (*). When R1 is —$CH_3$, preferred compounds have the (R) configuration at this chiral center. When R1 is —$CF_3$, preferred compounds have the (S) configuration.

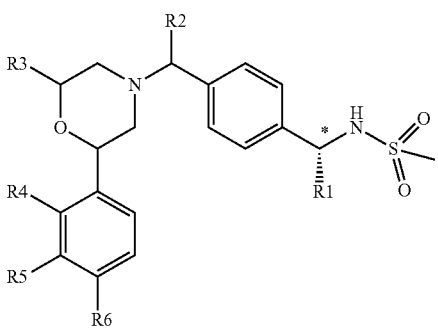

In one embodiment R1 is —$CH_3$. In another embodiment R1 is —$CF_3$.

Preferably R2 is H.
Preferable R3 is H.
Preferably R4 is selected from: H, —$OCH(CH_3)_2$, and halogen. More preferably R4 is selected from: H and halogen. Still more preferably R4 is selected from: H and Cl.
Preferably R5 is selected from: H, —$CF_3$—$OCH_3$, F, and Cl. More preferably R5 is selected from: H, —$CF_3$, F, and Cl. Still more preferably R5 is H.
Preferably R6 is selected from H and F. Preferably R6 is F.

The present invention provides a compound of Formula III below:

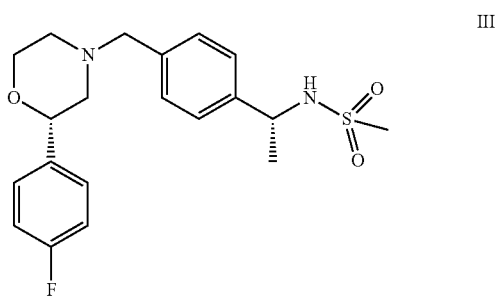 [SMILES: C[C@@H](NS(C)(=O)=O)c1ccc(CN2CCO[C@@H](c3ccc(F)cc3)C2)cc1]

or a pharmaceutically acceptable salt thereof.

The present invention provides a compound according either Formulae I or II wherein: R1 is —$CH_3$; R2 is selected from H and —$CH_3$; R3 is selected from H and —$CH_3$; R4 is selected from: H, —$OCH(CH_3)_2$, and halogen; R5 is selected from: H—$CF_3$, —$OCH_3$, Cl, and F; and R6 is selected from H or F; or a pharmaceutically acceptable salt thereof.

The present invention provides a compound according to either Formulae I or II wherein R1 is —$CH_3$; R2 is selected from H and —$CH_3$; R3 is selected from H and —$CH_3$; R4 is selected from: H, and halogen; R5 is selected from: H, —$CF_3$, F, and Cl; and R6 is selected from: H and F; or a pharmaceutically acceptable salt thereof.

The present invention provides a compound according to either Formulae I or II wherein: R1 is —$CH_3$; R2 is selected from: H and —$CH_3$; R3 is selected from: H and —$CH_3$; R4 is selected from: H and halogen; R5 is selected from: H, F, and Cl; and R6 is selected from H or F; or a pharmaceutically acceptable salt thereof.

The present invention provides a compound according to either Formula I or II wherein: R1 is —$CH_3$; R2 is H; R3 is H; R4 is selected from: H, and Cl; R5 is H, Cl, and F; and R6 is selected from H or F; or a pharmaceutically acceptable salt thereof.

The present invention provides a compound according to either Formula I or II wherein: R1 is —$CH_3$; R2 is H; R3 is H; R4 is selected from: H, and Cl; R5 is H; and R6 is selected from H or F; or a pharmaceutically acceptable salt thereof.

The present invention provides a compound according to either Formula I or II wherein: R1 is —$CH_3$; each of R2, R3, R4, and R5 is H; and R6 is F.

The present invention provides a compound according either Formulae I or II wherein: R1 is —$CF_3$; R2 is selected from H and —$CH_3$; R3 is selected from H and —$CH_3$; R4 is selected from: H, —$OCH(CH_3)_2$, and halogen; R5 is selected from: H—$CF_3$, —$OCH_3$, Cl, and F; and R6 is selected from H or F; or a pharmaceutically acceptable salt thereof.

The present invention provides a compound according to either Formulae I or II wherein R1 is —$CF_3$; R2 is selected from H and —$CH_3$; R3 is selected from H and —$CH_3$; R4 is selected from: H, and halogen; R5 is selected from: H, —CF₃, F, and Cl; and R6 is selected from: H and F; or a pharmaceutically acceptable salt thereof.

The present invention provides a compound according to either Formulae I or II wherein: R1 is —CF₃; R2 is selected from: H and —CH₃; R3 is selected from: H and —CH₃; R4 is selected from: H and halogen; R5 is selected from: H, F, and Cl; and R6 is selected from H or F; or a pharmaceutically acceptable salt thereof.

The present invention provides a compound according to either Formula I or II wherein: R1 is —CF₃; R2 is H; R3 is H; R4 is selected from: H, and Cl; R5 is H. Cl, and F; and R6 is selected from H or F; or a pharmaceutically acceptable salt thereof.

The present invention provides a compound according to either Formula I or II wherein: R1 is —CF₃; R2 is H; R3 is H; R4 is selected from: H, and Cl; R5 is H; and R6 is selected from H or F; or a pharmaceutically acceptable salt thereof.

The present invention provides a compound according to either Formula I or II wherein: R1 is —CF₃; each of R2, R3, R4, and R5 is H; and R6 is F.

Preferably the pharmaceutically acceptable salt is selected from: a chloride salt and a maleate salt. More preferably the pharmaceutically acceptable salt is maleate salt.

Preferred compounds are N-[(1R)-1-(4-{[(2S)-2-(4-Fluorophenyl)morpholin-4-yl]methyl}phenyl)ethyl]methanesulfonamide;

N-[(1R)-1-(4-{[(2S)-2-(4-Fluorophenyl)morpholin-4-yl]methyl}phenyl)ethyl]methanesulfonamide hydrochloride; and N-[(1R)-1-(4-{[(2S)-2-(4-Fluorophenyl)morpholin-4-yl]methyl}phenyl)ethyl]methanesulfonamide maleic acid.

The present invention provides a pharmaceutical composition comprising a compound of Formulae I, II, or III as described above or a pharmaceutically acceptable salt thereof, and at least one of a pharmaceutically acceptable carrier, diluent, or excipient.

The present invention also provides a method of treating a patient in need of treatment for hypertriglyceridemia, the method comprises administering to the patient an effective amount of a compound, according to Formulae I, II, or III above.

The present invention provides a compound, according Formulae I, II, or III above for use in the treatment of hypertriglyceridemia.

The present invention provides for the use of a compound according Formulae II, or III above in the manufacture of a medicament to treat hypertriglyceridemia.

The term "pharmaceutically-acceptable salt" refers a salt of the compound of the invention considered to be acceptable for clinical and/or veterinary use. Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

Pharmaceutical formulations of the present invention may be prepared by procedures known in the art using known or readily available additives. The term "pharmaceutically acceptable carrier, diluent, or excipient" as used herein refers to one or more carriers, diluents, and excipients that are compatible with the other ingredients of the formulation and not deleterious to a patient. Pharmaceutical compositions and processes for their preparation are known in the art and examples can be found in Remington, "The Science and Practice of Pharmacy" (A. Gennaro, et al. eds. 19$^{th}$ ed. Mack Publishing Co.) Non-limiting examples of pharmaceutically acceptable carriers, excipients, and diluents are suitable for such formulations include the following: starch, sugars, mannitol, and silica derivatives; binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate.

As used herein patient refers to an animal in need of treatment, preferably not exclusively a mammal, which is preferably a human; or alternatively a companion animal. such as a dog or cat; or a fowl.

Unless noted to the contrary, the compounds illustrated herein are named and numbered using either ACDLABS or Symyx Draw 3.2.

GENERAL CHEMISTRY

As used herein, the following terms have the meanings indicated: "ACN" refers to actonitrile; "DCM" refers to dichloromethane; "DEA" refers to diethylamine; "DMEA" refers to dimethylethylamine; "DMF" refers to dimethylformamide; "ee" refers to enantiomeric excess; "EtOAc" refers to ethyl acetate; "EtOH" refers to ethanol; "h" refers to hour(s); "HPLC" refers to high performance liquid chromatography; "IPA" refers to isopropyl alcohol; "Isomer 1" refers to the first eluting isomer; "Isomer 2" refers to the second eluting isomer; "LC/MS" refers to liquid chromatography followed by mass spectroscopy; "MeOH" refers to methanol; "min" refers to minute(s); "MS" refers to mass spectroscopy; "NMR" refers to nuclear magnetic resonance; "SFC" refers to supercritical fluid chromatography; "THF" refers to tetrahydrofuran.

Scheme 1

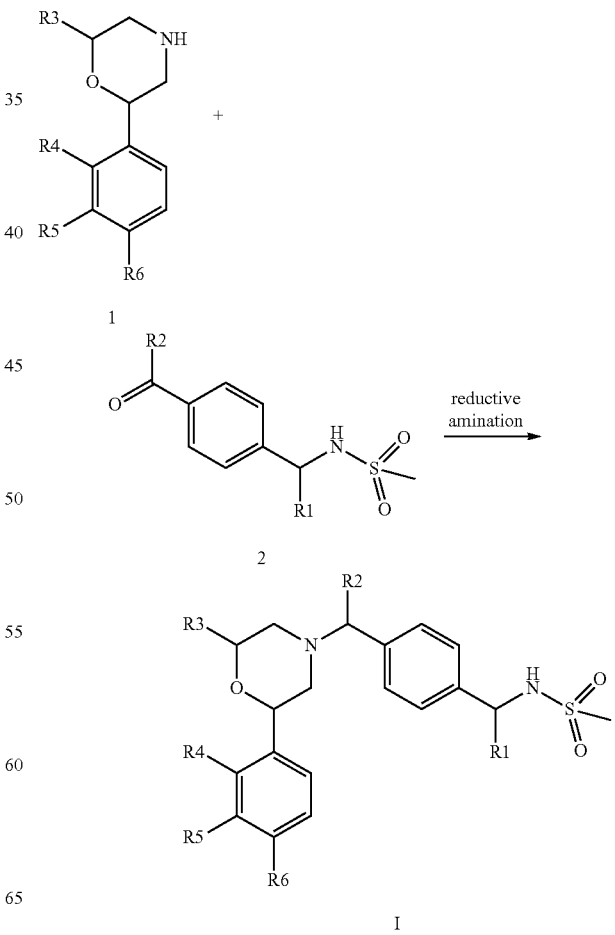

Scheme 1 illustrates the general synthesis of compound of Formula I.

A substituted morpholine compound 1, which is either commercially available or synthesized by known literature methods, reacts with an aldehyde or ketone 2 under reductive amination conditions to provide the compound of Formula I. ((See: Richard C. Larock, *Comprehensive Organic Transformations: a guide to functional group preparations*, 2nd edition, Page 835-846, Wiley-VCH, (1999)). Preferably, morpholine compound 1 reacts with compound 2 with the existence of a reducing agent such as triacetoxyborohydride and an acid such as acetic acid in dichloromethane to provide the compound of Formula I. which can be converted to a suitable salt with appropriate acids, for example, HCl to form the hydrochloride salt.

Preparation 1

(N—Z)—N-[(4-Bromophenyl)methylene]-(R)-2-methyl-propane-2-sulfinamide

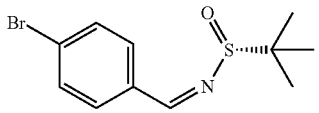

Add (R)-2-methylpropane-2-sulfinamide (40.5 g, 0.33 mol) portion-wise to a solution of 4-bromobenzaldehyde (65.57 g, 0.35 mol) in toluene (283 mL). Stir the mixture at ambient temperature for 15 minutes and then add sodium hydroxide (1.34 g, 0.33 mol). Stir the suspension at ambient temperature for 12 h. Add sodium sulphate (16 g) and Celite® (16 g) and stir the suspension for 15 min. Filter and concentrate the filtrate under reduced pressure. Purify the residue by silica gel chromatography eluting with hexane/EtOAc (100% to 70% hexane) to afford the title compound as a white solid (85.5 g, 88% yield). MS (m/z): 288 (M+1).

Preparation 2

N-[(1S)-1-(4-Bromophenyl)-2,2,2-trifluoro-ethyl]-(R)-2-methyl-propane-2-sulfinamide

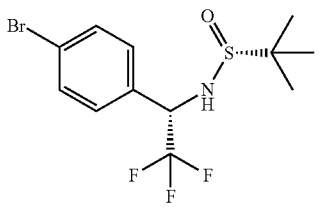 [SMILES: CC(C)(C)[S@@](=O)N[C@@H](c1ccc(Br)cc1)C(F)(F)F]

Add neat (trifluoromethyl)trimethylsilane (109 mL, 0.74 mol) at 0° C. to a stirred solution of tetrabutylammonium acetate (88 g, 0.29 mol) and (N—Z)—N-[(4-bromophenyl)methylene]-(R)-2-methyl-propane-2-sulfinamide (85 g, 0.29 mol) in DMF (1.2 L) at 0° C. Stir the mixture at 0-5° C. for 90 min. Add saturated aqueous ammonium chloride solution (1.2 L) and extract with EtOAc (4×400 mL). Combine the extracts and sequentially wash the extracts with water then brine (2×1 L); dry over magnesium sulphate; filter; and concentrate the filtrate under reduced pressure. Triturate the residue with hexane (200 mL) for 10 minutes, filter and dry the filtrate under reduced pressure to afford the title compound as a yellow solid (81 g, 76% yield, >98 de). MS (m/z): 358 (M+1).

Preparation 3

(1S)-1-(4-Bromophenyl)-2,2,2-trifluoroethanamine

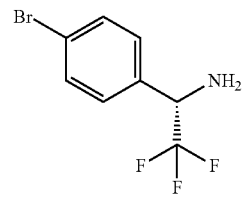 [SMILES: N[C@@H](c1ccc(Br)cc1)C(F)(F)F]

Add HCl (4M in dioxane, 226 mL, 0.9 mol) to a suspension of N-[(1S)-1-(4-bromophenyl)-2,2,2-trifluoro-ethyl]-(R)-2-methyl-propane-2-sulfinamide (81 g, 0.23 mol) in MeOH (670 mL). Stir the mixture at ambient temperature for one hour. Remove the solvent under reduced pressure and triturate the residue with methyl tert-butyl ether (200 mL) for 10 min to give the HCl salt as a brown solid. Dissolve the salt in water (1.2) and sufficient add 2N NaOH solution to raise the pH of the aqueous solution to a pH of 10. Extract the mixture with methyl tert-butyl ether (3×500 mL). Wash the organic phase with water then brine (500 mL each); dry over magnesium sulphate; filter; and concentrate the filtrate under reduced pressure to give the title compound as a yellow solid (46 g, 80% yield, 98% ee). MS (m/z): 358 (M+1).

Preparation 4

N-[(1S)-1-(4-Bromophenyl)-2,2,2-trifluoro-ethyl]methanesulfonamide

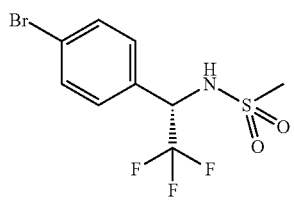 [SMILES: CS(=O)(=O)N[C@@H](c1ccc(Br)cc1)C(F)(F)F]

Add methanesulfonyl chloride (16.42 mL, 0.21 mol) dropwise to a mixture of (1S)-1-(4-bromophenyl)-2,2,2-trifluoroethanamine (49 g, 0.19 mol), 4-dimethylaminopyridine (1.18 g, 9.0 mmol), 2,6-lutidine (67 mL, 0.57 mol) in DCM (250 mL) at 0° C. Warm the mixture to ambient temperature and stir at that temperature for 20 hours. Dilute the reaction mixture with DCM (300 mL) and wash it sequentially with 2M HCl (2×200 mL), water (250 mL), then brine (250 mL). Collect the organic phase and dry over magnesium sulphate; filter; and concentrate the filtrate under reduced pressure. Triturate the residue with hexane (200 mL) for 10 min; filter; and dry the solid under reduced pressure to give the title compound as a pale brown solid (60 g, 93% yield, 98% ee). MS (m/z): 332 (M+1).

Preparation 5

N-[(1S)-2,2,2-Trifluoro-1-(4-formylphenyl)ethyl]
methanesulfonamide

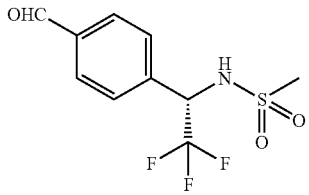 [SMILES: CS(=O)(=O)N[C@@H](c1ccc(C=O)cc1)C(F)(F)F]

Add N-[(1S)-1-(4-bromophenyl)-2,2,2-trifluoro-ethyl] methanesulfonamide (30 g, 90 mmol), palladium(II) acetate (0.81 g, 3.6 mmol), butyldi-1-adamantylphosphine (3.89 g, 10.84 mmol) and tetramethylethylenediamine (10.50 g, 90 mmol) in toluene (1.5 mL) to a 2 L PARR reactor. Seal the reactor and pressure it with synthesis gas (1:1 $CO/H_2$ at 75 psi). Stir the reaction mixture for 16 h while maintaining the temperature at 95° C. Cool the mixture; vent; and open the reactor. Filter the mixture through Celite® and concentrate the filtrate under reduced pressure. Purify the crude residue by silica gel chromatography eluting with hexane/EtOAc (8:2 to 1:1) to afford the title compound (22.8 g, 90%, 80% ee). Enrich the chiral purity of the compound by eluting it through a chiral column: Chiralpak AS-H (2.1×25 cm, 5 uM) $CO_2$/EtOH (9:1) to provide the title compound (19 g, 75% yield, 98% ee). MS (m/z): 282 (M+1).

Preparation 6

N-[(1R)-1-(4-Bromophenyl)ethyl]methanesulfonamide

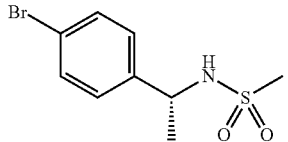

Add methanesulfonyl chloride (13.44 mL, 0.17 mmol) to a mixture of (1R)-1-(4-bromophenyl)ethanamine (25 g, 0.12 mol) and triethylamine (51 mL, 0.36 mol) in DCM (250 mL) at 0° C. Warm to ambient temperature and stir for 2.5 h. Wash reaction mixture with 2M aqueous HCl (100 ml). Then sequentially wash the organic phase with water then brine (2×100 mL). Dry the organic phase over anhydrous sodium sulphate; filter; and concentrate the filtrate under reduced pressure to give a residue. Triturate the residue with hexane (150 mL); filter; and dry under reduced pressure to afford the title compound as a yellow solid (33.24 g, 96%, ee>98%). MS (m/z): 278 (M+1).

Preparation 7

N-[(1R)-1-(4-Formylphenyl)ethyl]methanesulfonamide

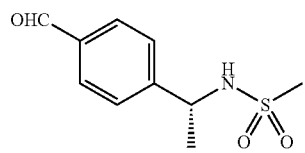

Combine N-[(1R)-1-(4-bromophenyl)ethyl]-methanesulfonamide (10 g, 35 mmol), (1,1'-bis(diphenylphosphino)-ferrocene)palladium(II) chloride (733 mg, 0.9 mmol), sodium carbonate (3.81 g, 35 mmol) and DMF (50 mL) in a 300 mL PARR reactor. Add triethylsilane (11.6 mL, 0.72 mmol) and purge the reactor with carbon monoxide three times. Charge the reactor with carbon monoxide (50 psi) and stir the mixture at 90° C. for 15 h. Cool the reactor to ambient temperature; open; filter mixture through a Celite® pad; and wash the pad with DCM (150 mL). Sequentially wash the filtrate with water then brine (2×80 mL). Concentrate the organic phase under reduced pressure to obtain the residue as an orange oil. Purify the orange oil by silica gel flash chromatography eluting with hexane/EtOAc (0 to 30% EtOAc) to provide the title compound (5.6 g, 70%, ee>98%). MS (m/z): 228 (M+1).

Preparation 8

(1S)-2-Bromo-1-(4-fluorophenyl)ethanol

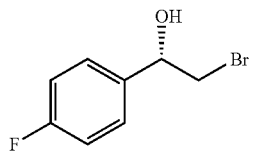

Under a nitrogen atmosphere, charge a 30 liter round bottom flask with a solution of (S)-1-methyl-3,3-diphenyl-3a,4,5,6-tetrahydropyrrolo[1,2-c][1,3,2]oxazaborole (1 M in toluene; 44 mL; 44 mmol) at 22° C. Add a solution of borane-N,N-diethylaniline complex (1230 g; 7540 mmol) in methyl t-butyl ether (4.5 L). Heat and maintain the mixture at 40° C. for 30 min. Add a solution of bromo-4-fluoroacetophenone (1640 g; 7530 mmol) in methyl t-butyl ether (4.5 L) drop-wise over 30 min. Stir the mixture at 40° C. for 2 hours. Cool to 10° C. using an ice water bath; then slowly add MeOH (590 mL) to quench the reaction. Stir the mixture for 30 min while maintaining it at 10-20° C. Add hydrochloric acid (3.0 M, 7.5 L) to the mixture while it is at 10° C. Stir for one hour and filter. Collect the filtrate. Separate the layers in the filtrate; extract the aqueous phase with methyl tert-butyl ether (1×3 L); combine the organic phases and wash with brine; dry over $Na_2SO_4$; and filter; and remove the volatiles from the filtrate under reduced pressure to give the title compound as a pale yellow oil (1650 g, 99%). MS (m/z): 201 (M-OH); ee value: 97.5% (AD-H 250 mm×4.6 mm×5 μm column using 99:1 hexanes:EtOH at 25° C. with a flow rate of 1.0 mL/min).

Preparation 9

(S)-2-(4-Fluorophenyl)oxirane

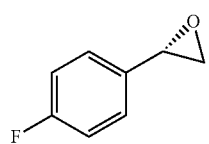

Dissolve (1S)-2-bromo-1-(4-fluorophenyl)ethanol (1650 g, 7.53 mol) in 6.8 L of methyl tert-butyl ether. Add NaOH (2M, in $H_2O$; 4.93 L) while the mixture is at 20° C. Stir the mixture for 3 h while maintaining it at 20-22° C. Separate the layers and extract the aqueous layer with methyl tert-butyl ether (1×2 L). Combine the organic phases; wash the organic phases with brine (1×2 L); dry over Na$_2$SO$_4$; and filter; concentrate the filtrate to give a residue. Purify via silica gel flash column chromatography using a 50:1 mixture of petroleum ether:EtOAce to elute the product. Concentrate the product fractions to give the title compound as a pale yellow oil (880 g, 84%). $^1$H NMR (300 MHz, CDCl$_3$): 7.27-7.21 (m, 2H), 7.06-7.01 (m, 2H), 3.86 (dd, J=2.6, 4.0 Hz, 1H), 3.16 (dd, J=4.1, 5.5 Hz, 1H), 2.79 (dd, J=2.6, 5.4 Hz, 1H); ee value: 97.5% (AD-H 250 mm×4.6 mm×5 μm column using 99:5 hexanes:ethyl alcohol at 25° C. with a flow rate of 1.0 mL/min).

Preparation 10

(1S)-2-(Benzylamino)-1-(4-fluorophenyl)ethanol

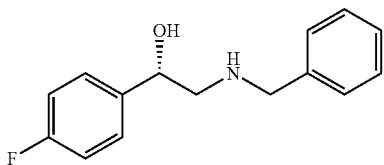 [SMILES: O[C@H](CNCc1ccccc1)c1ccc(F)cc1]

Charge a 10 L round bottom flask with (S)-2-(4-fluorophenyl)oxirane (880 g, 6.38 mol) under a nitrogen atmosphere. Add benzylamine (2047 g, 19.13 mol) while the mixture is maintained at 20° C. Heat the mixture to 80° C. and stir it at that temperature for 5 h. Cool to 22° C. and stir for 16 h. Add H$_2$O (3 L) to quench the reaction. Filter and wash the filter cake with water (2×1 L). Slurry the solid obtained with heptane (2 L) and filter to give the title compound (1216 g, 77%). MS (m/z): 246 (M+1); ee value: 99.0% (AD-H 250 mm×4.6 mm×5 μm column using 90:10 hexanes (with 0.02% diethylamine):EtOH at 25° C. with a flow rate of 1.0 mL/min).

Preparation 11

N-Benzyl-2-chloro-N-[(2S)-2-(4-fluorophenyl)-2-hydroxyethyl]acetamide

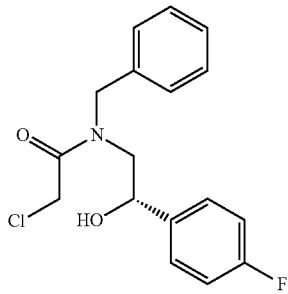 [SMILES: O=C(CCl)N(Cc1ccccc1)C[C@@H](O)c1ccc(F)cc1]

Dissolve (1S)-2-(benzylamino)-1-(4-fluorophenyl)ethanol (1215 g, 4.96 mol) in 12.15 L DCM and cool the mixture to 0° C. Add NaOH (1M in H$_2$O, 5.46 L, 5.46 mol) dropwise over 30 min. Stir the mixture vigorously for 10 min while maintaining it at 0-3° C.; then add a solution of chloroacetyl chloride (616.5 g, 5.46 mol) in 4.86 L of DCM dropwise over 1 h keeping the temperature below 6° C. Stir the mixture for 1 h at 0° C.; separate the layers; and extract the aqueous phase with DCM (1×2 L). Combine the organic layer and extracts; wash them with 10% hydrochloric acid (1.5 L), water (1.5 L) and 1M NaOH (1 L). Dry over Na$_2$SO$_4$ and filter. Collect the filtrate and remove the solvent under reduced pressure to provide the title compound as a colorless oil (1440 g, 90%). MS (m/z): 322 (M+1).

Preparation 12

(6S)-4-Benzyl-6-(4-fluorophenyl)morpholin-3-one

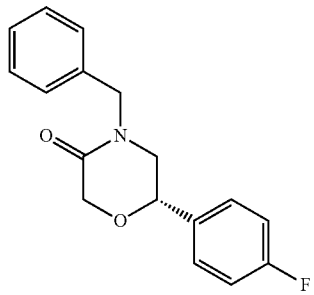 [SMILES: O=C1CO[C@@H](c2ccc(F)cc2)CN1Cc1ccccc1]

Add N-benzyl-2-chloro-N-[(2S)-2-(4-fluorophenyl)-2-hydroxyethyl]acetamide (1440 g, 4.48 mol) to tert-butyl alcohol (14.5 L) and add potassium tert-butoxide (753 g, 6.73 mol) portion-wise while maintaining the mixture at 22° C. Maintain the mixture at 22° C. and stir for 1.5 hours. Add a saturated aqueous solution of ammonium chloride (1306 g) to quench the reaction. Stir for an additional 1 hour and then add H$_2$O (2 L). Extract with EtOAc (2×10 L); combine the extracts; and concentrate the extracts under reduced pressure provide a residue. Re-dissolve the residue in EtOAc (20 L) and wash with H$_2$O (10 L). Dry the EtOAc solution over Na$_2$SO$_4$ and filter. Collect the filtrate and remove the solvent under reduced pressure to provide the title compound as a colorless oil (1250 g, 98%). MS (m/z): 286 (M+1).

Preparation 13

(2S)-4-Benzyl-2-(4-fluorophenyl)morpholine

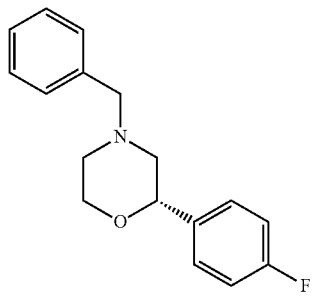 [SMILES: Fc1ccc([C@H]2CN(Cc3ccccc3)CCO2)cc1]

Under a nitrogen atmosphere, drop-wise add a solution of (6S)-4-benzyl-6-(4-fluorophenyl) morpholin-3-one (625 g, 2.19 mol) in THF (22 L) to lithium aluminum hydride in THF (1M in THF, 5.0 L, 5 mol) while maintaining the temperature at 20° C. Heat the mixture to 70° C. and stir for 1.5 h. Cool the mixture to 0° C. and add H$_2$O (200 mL) to quench the reaction, followed by aqueous NaOH (4 M, 1.25 L), then add more H$_2$O (600 mL). Stir the resulting mixture for 30 min; filter; and rinse the solid with EtOAc (10 L). Collect the filtrate and concentrate it under reduced pressure to provide the title compound (561 g, 94%). MS (m/z): 272 (M+1).

Preparation 14

(2S)-2-(4-fluorophenyl)morpholine hydrochloride

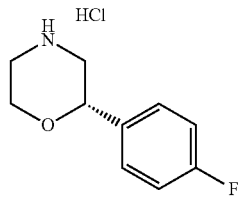 [SMILES: Cl ; Fc1ccc([C@H]2CNCCO2)cc1]

Dissolve (2S)-4-benzyl-2-(4-fluorophenyl)morpholine (948 g, 3.5 mol) in 1,2-dichloroethane (17 L). Heat the mixture to 70° C. and add 1-chloroethyl chloroformate (1500 g, 10.5 mol) drop-wise while heating. Stir the mixture at 70° C. for 3 h and then concentrate the mixture to give a residue. Dissolve the residue in MeOH (10 L) and heat to 70° C. while stirring for 1 h. Concentrate the solution under reduced pressure to give a residue. Slurry the residue with EtOAc (5 L); filter; and wash the solid with EtOAc (1 L) to provide an off white solid. Slurry the solid with 10:1 EtOAc/MeOH (10:1. 3 L); filter; collect the solid to provide the title compound as a white solid (300 g). Concentrate the mother liquor to provide additional material. Slurry the this material with a mixture of EtOAc/MeOH (2:1; 1 L) and filter to give an additional 105 g of the title compound as a white solid. Mix the product batches to give the title compound (405 g, 53%). MS (m/z): 182 (M-Cl). ee value 100% (AD-H 250 mm×4.6 mm×5 um column using 90:10 hexanes (with 0.02% DEA):ethyl alcohol at 25° C. with a flow rate of 1.0 mL/min).

Preparation 15

2-Bromo-1-(2-isopropoxyphenyl)ethanone

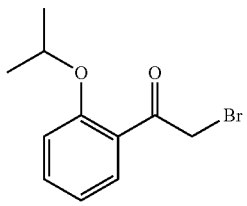

Dissolve 1-(2-isopropoxyphenyl)ethanone (1.0 g, 6 mmol) in Et$_2$O (25 mL) and add bromine (0.3 mL, 6 mmol) drop-wise while stirring stir the mixture in the dark at ambient temperature. Wash the reaction mixture with a saturated aqueous Na$_2$CO$_3$ solution. Dry it over MgSO$_4$; filter; collect the filtrate; removed the volatiles under reduced pressure to provide the title compound (1.5 g, 83%). MS (m/z): 258 (M+1).

Preparation 16

4-Benzyl-2-(2-chloro-4-fluoro-phenyl)morpholine

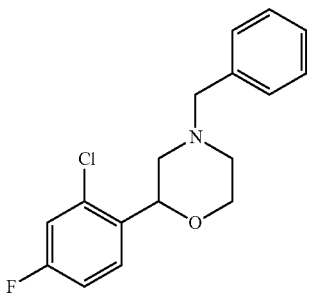 [SMILES: Fc1ccc(C2CN(Cc3ccccc3)CCO2)c(Cl)c1]

Combine formic acid (98-100%; 0.30 mL, 8 mmol) and 2-benzylaminoethanol (1.21 g, 8 mmol) and cool the resulting mixture with an ice bath. Add 2-bromo-1-(2-chloro-4-fluoro-phenyl)ethanone (1.0 g, 4 mmol); heat the mixture to reflux; and stir at that temperature for 20 h. Dilute the mixture with DCM and wash with saturated aqueous Na$_2$CO$_3$ solution. Dry organic phases over MgSO$_4$; filter; collect the filtrate; and concentrate under reduced pressure. Purify via flash column chromatography eluting with a gradient of 0-20% methyl tertiary-butyl ether in hexanes. Combine the product fractions and remove the solvents under reduced pressure to give the title compound as a yellow oil (1.22 g, 43%). MS (m/z): 306 (M+1).

Preparation 17

4-Benzyl-2-(2-isopropoxyphenyl)morpholine

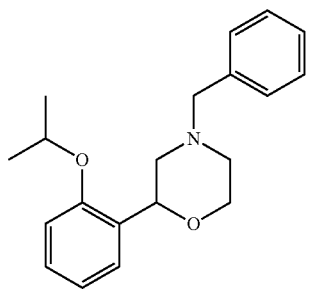 [SMILES: CC(C)Oc1ccccc1C1CN(Cc2ccccc2)CCO1]

Prepare 4-benzyl-2-(2-isopropoxyphenyl)morpholine essentially by the method of Preparation 16. MS m/z 312 (M+1)

Preparation 18

2-(6-Chloro-4-fluoro-cyclohexa-2,4-dien-1-yl)morpholine

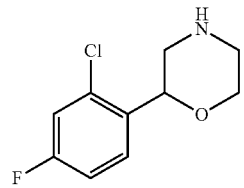 [SMILES: Fc1ccc(C2CNCCO2)c(Cl)c1]

Dissolve 4-benzyl-2-(2-chloro-4-fluoro-phenyl)morpholine (529 mg, 1.73 mmol) in DCM (2.5 mL). Add 1-chloroethyl chloroformate (1.25 g, 8.65 mmol); heat to 80° C.; and stir overnight. Add MeOH (2.5 mL) and stir at 65° C. for 3 hours. Concentrate under reduced pressure and purify via SCX chromatography eluting with a gradient of 0-100% of (2N NH$_3$/MeOH) in MeOH. Combine the product fractions and remove the solvents under reduced pressure to provide the title compound as a white solid (345 mg, 92%). MS (m/z): 216 (M+1).

Preparation 19

2-(2-Isopropoxyphenyl)morpholine

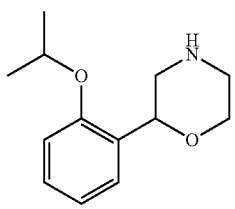 [SMILES: CC(C)Oc1ccccc1C1CNCCO1]

Under a nitrogen atmosphere combine 4-benzyl-2-(2-isopropoxyphenyl)morpholine (0.51 g, 2 mmol), 10% PdOH/Carbon (0.51 g, 10 mol %) and anhydrous ammonium formate (0.53 g, 10 mmol). Heat the resulting mixture to reflux and stir. Monitor the progress of the reaction via thin layer chromatography. After completion, filter reaction mixture through a pad of Celite®; collect the filtrate; and remove the solvent under reduced pressure to give the title compound as an oil (0.25 g, 63%). MS (m/z): 433 (M+1).

Preparation 20

N-[2-[2-Bromo-1-(3-methoxyphenyl)ethoxy]ethyl]-4-nitro-benzenesulfonamide

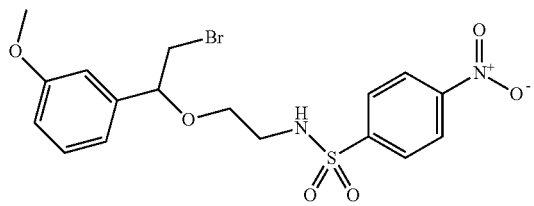

Add ethylene oxide (11 mL, 220 mmol) all at once to DCM cooled to 0° C.; then add 1-methoxy-3-vinylbenzene (7.09 g, 52.82 mmol) via a syringe. Stir the mixture while maintaining it 0° C. Add N-bromosuccinimide (9.4 g, 52.82 mmol) and 4-nitrobenzenesulfonamide (8.9 g, 44.02 mmol). Wrap flask in foil and stir the reaction mixture for 20 h while maintaining it at ambient temperature. Concentrate under reduced pressure; filter; and concentrate the filtrate under reduced pressure to provide a residue. Purify the residue via flash column chromatography eluting with a 5-40% gradient of EtOAc in hexanes. Combine the product fractions, and remove the solvents under reduced pressure to provide the title compound as a dark yellow oil (14.22 g, 70.3%). MS (m/z): 459 (M+1).

Preparation 21

2-(3-Methoxyphenyl)-4-(4-nitrophenyl)sulfonyl-morpholine

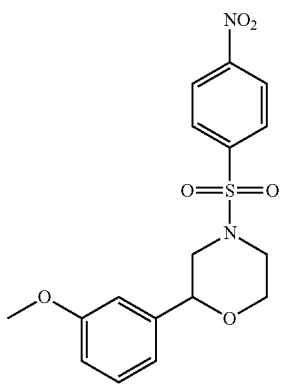 [SMILES: COc1cccc(C2CN(S(=O)(=O)c3ccc([N+](=O)[O-])cc3)CCO2)c1]

Dissolve N-[2-[2-bromo-1-(3-methoxyphenyl)ethoxy] ethyl]-4-nitro-benzenesulfonamide (14.22 g, 30.96 moles) in ACN (200 mL); add potassium carbonate (6.42 g, 46.44 mmol); and heat the mixture to reflux. Stir the mixture for 3 h while refluxing. Cool the resulting mixture to ambient temperature and dilute it with EtOAc. Filter through Celite®; concentrate the filtrate under reduced pressure to provide a residue. Purify the residue via flash column chromatography eluting with a 50-80% gradient of EtOAc in hexanes. Combine the product fractions and remove the solvents under reduced pressure to provide the title compound as an orange solid (11.2 g, 95.6%). MS (m/z): 379 (M+1).

Preparation 22

2-(3-Methoxyphenyl)morpholine

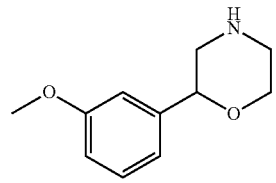

Dissolve 2-(3-methoxyphenyl)-4-(4-nitrophenyl)sulfonyl-morpholine (11.2 g, 29.6 mmol) in ACN (150 mL) and water (2.67 mL). Add LiOH (6.21 g, 147.99 mmol) while stirring the mixture and followed by 1-propanethiol (13.42 mL, 147.99 mmol). Stir the mixture for 25 h at ambient temperature. Dilute the mixture with EtOAc and add brine. Extract twice with EtOAc. Collect and concentrate the extracts to ~200 mL under reduced pressure, then wash three times with 1N HCl. Combine the aqueous acid extracts and add $Na_2CO_3$ until the mixture is basic. Extract the basic solution three times with EtOAc; combine the extracts; wash the extracts with brine; and dry over $Na_2SO_4$. Filter; collect the filtrate; and remove the solvents under reduced pressure to provide a residue. Purify the residue via flash column chromatography eluting with EtOAc, followed by a 5-100% gradient of (10% 2M $NH_3$ in MeOH)/DCM. Combine the product fractions, and remove the solvents under reduced pressure to provide the title compound as a yellow oil (3.09 g, 15.99 mmol). MS (m/z): 194 (M+1).

Preparation 23

N-[(1R)-1-(4-Acetylphenyl)ethyl]methanesulfonamide

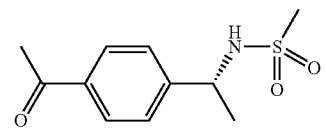 [SMILES: CC(=O)c1ccc([C@@H](C)NS(C)(=O)=O)cc1]

Charge a tube with N-[(1R)-1-(4-bromophenyl)ethyl] methanesulfonamide (29 g, 104 mmol), butyl vinyl ether (34.23 mL, 261 mmol), palladium(II) acetate (14.04 g, 63 mmol), bis-(1,3-diphenylphosphino)propane (52.7 g, 125 mmol) and potassium carbonate (17.3 g, 125 mmol). Degas the tube with nitrogen for 2 minutes, and then add $H_2O$ (69.5 mL) and DMF (69.5 mL). Seal the tube and stir at 110° C. for 20 h. Cool the reaction mixture to ambient temperature and add HCl (2N, 60 mL). Stir the mixture at ambient temperature for 10 min. Adjust the pH of the mixture to a pH of 7 using NaOH pellets; dilute with DCM (220 mL); filter through a Celite® pad; and sequentially wash the filtrate with aqueous $K_2CO_3$ (2×120 mL), brine (2×100 mL), and $H_2O$ (100 mL). Dry the mixture over $MgSO_4$; filter; and concentrate the filtrate under reduced pressure to provide a residue. Purify the residue via flash column chromatography eluting with EtOAc in hexanes (step gradient of 0, 5, 10, 20, 30 and finally 40% EtOAc). Combine the product fractions and remove the solvents under reduced pressure to give the title compound (17.6 g, 70.0%) as a yellow oil. MS (m/z): 242 (M+1).

Preparation 24

N-[(1R)-1-[4-(1-Hydroxyethyl)phenyl]ethyl]methanesulfonamide, isomer 2

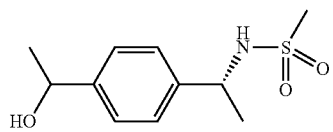

Dissolve N-[(1R)-1-(4-acetylphenyl)ethyl]methanesulfonamide (15 g, 62 mmol) in EtOH (155.4 mL) and cool with an ice bath. Add sodium borohydride (1.2 g, 31.1 mmol) and stir the resulting mixture in the ice bath for 2 h. Quench the reaction with H₂O (20 mL) and concentrate under reduced pressure. Dilute the residue with EtOAc (90 mL) and H₂O (50 mL). Separate the layers and wash the organic layer with brine (2×50 mL), dry over MgSO₄; filter; and concentrate the filtrate under reduced pressure to provide a residue. Purify and separate isomers using chromatography conditions K (see below) collecting the second eluting isomer as the title compound (2.01 g, 13%). MS (m/z): 261 (M+18).

EXAMPLE 1

N-[(1R)-1-(4-{[(2S)-2-(4-Fluorophenyl)morpholin-4-yl]methyl}phenyl)ethyl]methanesulfonamide

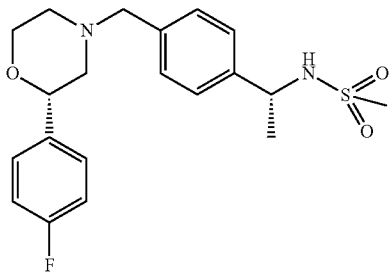 [SMILES: C[C@@H](NS(C)(=O)=O)c1ccc(CN2CCO[C@@H](c3ccc(F)cc3)C2)cc1]

Under a nitrogen atmosphere, suspend (2S)-2-(4-fluorophenyl)morpholine hydrochloride (29.5 g, 128.8 mmol) in DCM (17 L) at 22° C. and add triethylamine (35.89 mL, 257.5 mmol). Add N-[(1R)-1-(4-formylphenyl)ethyl]methanesulfonamide (29.26 g, 128.8 mmol) and stir the resulting solution for 30 min. Add acetic acid (8.85 mL, 154.5 mmol), then sodium triacetoxyborohydride (86.17 g, 386.3 mmol) portion-wise in 3 batches. Stir for 3 h; monitor the reaction via LCMS until completion. Quench the reaction via the slow addition of a saturated aqueous solution of sodium bicarbonate (259.31 mL) to give a solution with a pH of 8. Separate the layers, and extract the aqueous layer with 200 mL DCM. Combine the organic layers, wash with saturated sodium bicarbonate, water, brine, and then dry over MgSO₄. Filter; collect the filtrate; and concentrate to give a residue. Purify the residue via silica gel flash column chromatography, using a gradient of 100% DCM to DCM:MeOH (95:5). Combine the product fractions, and concentrate to provide the title product as a yellow thick oil (41 g, 81.13%). MS (m/z): 393 (M+1)

EXAMPLE 2

N-[(1R)-1-(4-{[(2S)-2-(4-Fluorophenyl)morpholin-4-yl]methyl}phenyl)ethyl]methanesulfonamide maleate

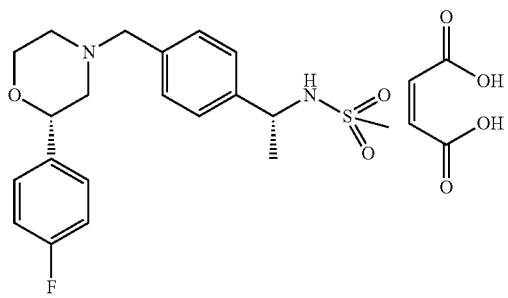

Method 1:
Dissolve N-[(1R)-1-(4-{[(2S)-2-(4-fluorophenyl)morpholin-4-yl]methyl}phenyl)ethyl]methanesulfonamide (250.47 mg) in EtOAc (10 mL). Add maleic acid (85 mg) dissolved in EtOAc (2 mL) at 60° C. Cool to ambient temperature and stir the mixture for 30 min. Filter the slurry and rinse with EtOAc (5 mL). Collect and dry the filter cake under reduced pressure to provide the title compound as a solid (280 mg, 97.7%). MS (m/z): 393 (M-maleic acid+1).

Method 2:
Dissolve N-[(1R)-1-(4-{[(2S)-2-(4-fluorophenyl)morpholin-4-yl]methyl}phenyl)ethyl]methanesulfonamide (270 g) in EtOAc (10 L). Heat the mixture to 60° C. and add maleic acid (96 g, 1.1 eq) in EtOAc (2.8 L). Allow the mixture to cool to ambient temperature and stir the resulted mixture for 14 h. Filter the slurry; rinse the solid with EtOAc (5 L); and dry the filter cake under reduced pressure. Dissolve the solid in 5 volumes of EtOH (1.4 L); heat at 90° C.; and add water (280 mL). Heat the mixture at 90° C. for 1 h, and then cool it to ambient temperature overnight. Filter the precipitate, dry in a vacuum oven at 40° C. to provide the title compound as a white solid (256 g, 70%). MS (m/z): 393 (M-maleic acid+1).

EXAMPLE 3

N-[(1R)-1-(4-{[(2S)-2-(4-fluorophenyl)morpholin-4-yl]methyl}phenyl)ethyl]methanesulfonamide hydrochloride

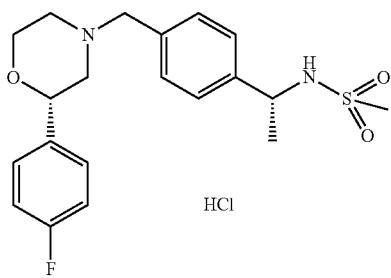

Dissolve N-[(1R)-1-(4-{[(2S)-2-(4-fluorophenyl)morpholin-4-yl]methyl}phenyl)ethyl]methanesulfonamide (50 g, 127.39 mmol) in isopropyl alcohol (200 mL). Add HCl (4M in dioxanes; 63.70 mL, 254.78 mmol) drop-wise to the solution and stir at ambient temperature for 50 min. Remove the volatiles under reduced pressure; add $H_2O$ (200 mL); then evaporate the water. Add $H_2O$ (200 mL) and isopropyl alcohol (100 mL), and concentrate to a total volume of 80 mL. Filter the resulting thick slurry; wash solid with $H_2O$; collect by filtration; and dry the filter cake under reduced pressure at 55° C. to provide the title compound as a white solid (40.6 g, 75%). MS (m/z): 393 (M-Cl).

EXAMPLE 4

N-[(1R)-1-(4-{1-[(2S)2-(4-fluorophenyl)morpholin-4-yl]ethyl}phenyl)ethyl]methanesulfonamide hydrochloride, Isomer 1

ABS

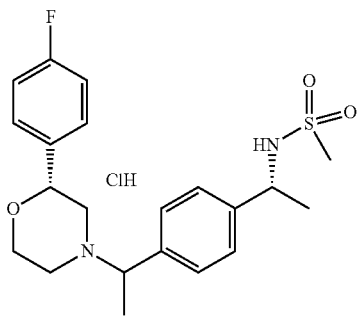

Isomer 1

Prepare N-[(1R)-1-(4-{1-[2-(4-fluorophenyl)morpholin-4-yl]ethyl}phenyl)ethyl]methanesulfonamide hydrochloride, isomer 1 essentially by the method of Example 3. MS (m/z) 407 (M-Cl)

EXAMPLE 5

N-[(1S)-1-(4-{[2-(2-chlorophenyl)morpholin-4-yl]methyl}phenyl)-2,2,2-trifluoroethyl]methanesulfonamide hydrochloride, Isomer 2

Isomer 2

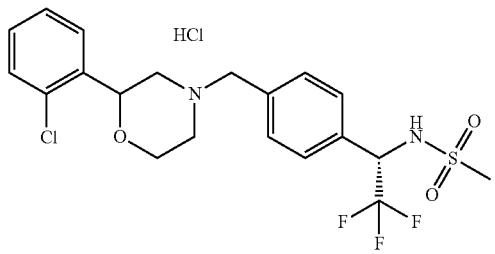

Combine 2-(2-chlorophenyl)morpholine, oxalic acid salt (200 mg, 0.696 mmol), triethylamine (193 µL, 1.39 mmol), N-[(1S)-2,2,2-trifluoro-1-(4-formylphenyl)-ethyl]-methanesulfonamide (205.3 mg, 0.73 mmol) and DCM (15 mL). Add acetic acid (47.8 µL, 0.83 mmol) and sodium triacetoxyborohydricle (465 mg, 2.09 mmol), and stir for 5 h at ambient temperature. Adjust the pH of the mixture to 10 with a saturated aqueous $NaHCO_3$ solution. Stir until gas evolution ceases; separate the layers; and extract the aqueous layer twice with DCM. Combine the organic extracts; wash them with brine; and dry over $MgSO_4$. Filter mixture; collect the filtrate; and concentrate it under reduced pressure to give a residue. Purify the residue on a 10 g SCX cartridge, wash the cartridge with DCM, 50% MeOH/DCM, 100% MeOH, then elute with $NH_3$ in MeOH (2N). Concentrate the product fractions under reduced pressure to provide the crude product as an oil. Purify the oil via chiral HPLC, using conditions E (see below) to provide the free base (104 mg, 32.3%) as the second eluting isomer. Dissolve the free base (104 mg, 0.224 mmol) in 1 mL DCM and add HCl in $Et_2O$ (2 M, 561.6 µL, 1.12 mmol) drop-wise. Stir at ambient temperature for 5 minutes and then remove the solvents under reduced pressure to give the title compound (99 mg, 88.2%). MS (m/z): 463 (M-Cl).

The following compounds are prepared essentially by the method of Example 5. All the following Examples in Table 1 are isolated as single isomers either starting from chiral starting materials and/or using the chromatographic columns and conditions identified below. The separation can be performed with the free base or with its salt form.

TABLE 1

| Ex # | Chemical name | Structure | MS (m/z): | Chrom Cond. |
|---|---|---|---|---|
| 6 | N-[(1R)-1-(4-{[2-(3-Fluorophenyl)morpholin-4-yl]methyl}phenyl)ethyl]methanesulfonamide hydrochloride, Isomer 1 | 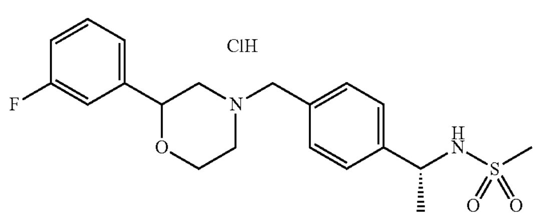 | 393 (M − Cl) | A |

Isomer 1
*HCl salt was used for separation.

TABLE 1-continued

| Ex # | Chemical name | Structure | MS (m/z): | Chrom Cond. |
|---|---|---|---|---|
| 7 | N-[(1R)-1-(4-{[2-(3-Methoxyphenyl)morpholin-4-yl]methyl}phenyl)ethyl]methanesulfonamide hydrochloride, Isomer 2 | Isomer 2 | 405 (M − Cl) | J |
| 8 | N-[(1R)-1-(4-{[2-(2-Choro-4-fluorophenyl)morpholin-4-yl]methyl}phenyl)ethyl]methanesulfonamide hydrochloride, Isomer 2 | Isomer 2 | 427 (M − Cl) | E |
| 9 | N-[(1R)-1-(4-{[2-(4-Chlorophenyl)morpholin-4-yl]methyl}phenyl)ethyl]methanesulfonamide hydrochloride, Isomer 2 | Isomer 2 | 409 (M − Cl) | B |
| 10 | N-{(1R)-1-[4-({2-[2-(1-Methylethoxy)phenyl]morpholin-4-yl}methyl)phenyl]ethyl}methanesulfonamide hydrochloride, Isomer 2 | Isomer 2 | 433 (M − Cl) | I |
| 11 | N-{(1R)-1-[4-({2-[3-(Trifluoromethyl)phenyl]morpholin-4-yl}methyl)phenyl]ethyl}methanesulfonamide hydrochloride, Isomer 2 | Isomer 2 | 443 (M − Cl) | C |

TABLE 1-continued

| Ex # | Chemical name | Structure | MS (m/z): | Chrom Cond. |
|---|---|---|---|---|
| 12 | N-[(1R)-1-(4-{[2-(3-Chlorophenyl)morpholin-4-yl]methyl}phenyl)ethyl]methanesulfonamide hydrochloride, Isomer 2 | Isomer 2 | 409 (M − Cl) | D |
| 13 | N-[(1R)-1-(4-{[(2R,6S)-2-Methyl-6-phenylmorpholin-4-yl]methyl}phenyl)ethyl]methanesulfonamide hydrochloride | 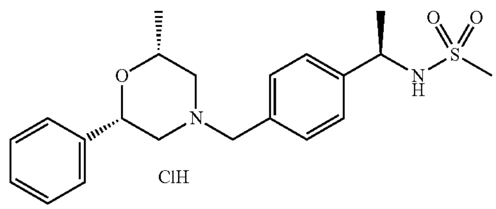 [SMILES: C[C@@H]1CN(Cc2ccc([C@@H](C)NS(C)(=O)=O)cc2)C[C@H](c2ccccc2)O1 ; Cl] | 389 (M − Cl) | |
| 14 | N-[(1S)-2,2,2-Trifluoro-1-(4-{[2-(4-fluorophenyl)morpholin-4-yl]methyl}phenyl)ethyl]methanesulfonamide hydrochloride, Isomer 1 | Isomer 1 | 447 (M − Cl) | F |
| 15 | N-[(1R)-1-(4-{[2-(2-Chlorophenyl)morpholin-4-yl]methyl}phenyl)ethyl]methanesulfonamide hydrochloride, Isomer 2 | Isomer 2 | 409 (M − Cl) | G |
| 16 | N-[(1R)-1-{4-[(2-Phenylmorpholin-4-yl)methyl]phenyl}ethyl]methanesulfonamide hydrochloride, Isomer 1 | Isomer 1 | 374 (M − Cl) | H |

EXAMPLE 17

N-[(1R)-1-[4-[1-[(2S)2-(4-Fluorophenyl)morpholin-4-yl]ethyl]phenyl]ethyl]methanesulfonamide, Isomer 1

ABS

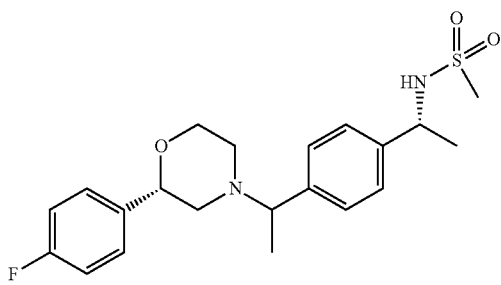 [SMILES: CC(c1ccc([C@@H](C)NS(C)(=O)=O)cc1)N1CCO[C@@H](c2ccc(F)cc2)C1]

Combine N-[(1R)-1-[4-(1-hydroxyethyl)phenyl]ethyl]-methanesulfonamide isomer 2 (420 mg, 1.73 mmol) and DCM (5 mL). Cool the mixture to 0° C. and it purge with nitrogen. Add acetyl bromide (295.8 µL, 3.45 mmol) and stir the reaction for 10 min while maintaining it at 0° C. Add an additional amount of acetyl bromide (519.5 µL, 6.90 mmol) and stir for an additional 10 min. Dilute the reaction with DCM, and evaporate solvents under reduced pressure to provide a residue. Dissolve the residue in DMF (2 mL) and add (2S)-2-(4-fluorophenyl)morpholine hydrochloride (71.1 mg, 0.327 mmol), $K_2CO_3$ (135.4 mg, 0.980 mmol) and stir at ambient temperature overnight. Filter the reaction, and purify the filtrate using SCX chromatography with an elution order of DCM, DCM/MeOH (1:1), MeOH, and finally 2M $NH_3$/MeOH. Combine the product fractions and remove the solvents under reduced pressure to provide a residue. Purify the residue via reverse phase HPLC (XTerra MS C18 column, pH 8) collecting the first eluting isomer (isomer 1) as the title compound (9.6 mg, 7.2%). MS (m/z): 407 (M+1).

Chromatography Conditions

TABLE 2

| Conditions | Column | Column Size | Mobile Phase |
|---|---|---|---|
| A | Chiralcel OD-H | 21 × 250 mm 5 um | 30% IPA (0.2% IPAm)/$CO_2$ |
| B | Chiralcel OJ-H | 21.2 × 250 mm 5 um | 20% MeOH (0.2% DMEA)/$CO_2$ |
| C | Chiralcel OD | 20 × 250 mm 10 um | 30% EtOH |
| D | Chiralcel OJ-H | 21.2 × 250 mm 5 um | 100% EtOH (0.2% DMEA) |
| E | Chiralpak AD-H | 21.2 × 250 mm 5 um | $CO_2$/EtOH-DEA (0.2%) 85/15 |
| F | Chiralcel OJ-H | 21.2 × 250 mm 5 um | 10% MeOH (0.2% DMEA)/$CO_2$ |
| G | Chiralpak AD-H | 21.2 × 250 mm 5 um | $CO_2$/EtOH-DMEA (0.2%) 80/20 |
| H | Chiralcel OD | 20 × 250 mm 10 um | (0.2% DMEA in EtOH) 100% |
| I | Chiralpak AD basic unit | 20 × 250 mm 10 um | 25% IPA/Hexanes |
| J | Chiralpak AD-H | 21.2 × 250 mm 5 um | $CO_2$/IPA-DMEA (0.2%) 80/20 |
| K | Chiralcel OJ-H × 2 | 21.2 × 250 mm 5 um | 8% MeOH/$CO_2$ |

MOGAT-2 Inhibitory Assay

The in vitro inhibitory activity of compounds against human MOGAT-2 is evaluated in this assay. MOGAT-2 transfers an oleoyl group to monooleoyl-glycerol ("MAG") from oleoyl-CoA to form dioleoyl-glycerol ("DAG") in the intestinal triglyceride resynthesis pathway. The assay takes advantage of Microscint E extraction, which extracts hydrophobic molecules selectively over hydrophilic ones to separate the $^{14}$C-oleoyl-CoA from $^{14}$C-DAG.

Genetically engineered insect SF9 cells express human MOGAT-2. Prepare the cell lysate in 20 mM of NaCl with protease inhibitor (Roche Cat#11873580001). Homogenize the SF9 cells expressing human MOGAT-2 at 15,000 rpm for 20×2 seconds (PT-3100 Polytrone). Centrifuge the homogenate at 1000 g for 10 minutes at 4° C. Collect the supernatant into a separate tube for protein quantification and activity testing. Purify the glycerol monooleate substrate (Spectrum Chemical, CAS#25496-72-4) chromatographically. Prepare the monoacylglycerol (MAG) substrate in phospholipid vescicles (dioleoyl phosphatidylcholine "DOPC"). Prepare the MAG/DOPC vesicles at 20 mM concentration of total lipids (MAG and DOPC). Prepare different molar ratios of MAG to total lipids for either compound screening (8.9%) or compound kinetic studies (2.6-40%). Mix the appropriate amount of purified MAG and DOPC (Avanti Polar Lipids #850375C) in chloroform in a glass tube. Subsequently, evaporate chloroform under stream of $N_2$ gas and then dry under reduced pressure for 30 minutes. Add an appropriate amount of buffer (Tris-Cl pH 7.4, 250 mM sucrose, 1 mM EDTA) to the dried MAG/DOPC mixture for the desired total lipid concentration. Sonicate the MAG/DOPC solution until the solution is clear. Measure the vesicle size using dynamic light scattering to confirm uniformity.

The assay buffer consists of 100 mM Tris, pH 7.5 (Invitrogen 15567-022), 11% DMSO, 250 mM sucrose (Sigma S-0389), 1 mM, EDTA, and Complete Protease Inhibitor cocktail (Roche Diagnostic 12454800). Add the test compounds to the buffer together with the substrates and enzymes. The final concentration for the reaction is 0.016 mg/mL SF9 cell extract, 20 µM oleoyl-CoA (3.5 µM $^{14}$C-oleoyl-CoA), 1.26 mM total lipid in the form of sonicated vesicles, composed of 8.9:91.1 (molar ratio) MAG:DOPC.

Stop the reaction after 90 minutes of incubation at room temperature by adding AESSM (12.5% of 100% denatured EtOH; 11% DI H2O; 2.5% 1.0N NaOH; 59% Isopropanol (Mallinckrodt 3031-08); 15% Heptane (Omni Solv HX0078)), by volume. Add Microscint E and then seal the plates and count on a scintillation counter after at least 4 hours of equilibration at room temperature. Calculate the $IC_{50}$ (concentration to reach half maximum inhibition) using Excel Fit software (version 4; Data analyzing using a 4-parameter non-linear logistic equation (ABase Equation 205)) by plotting concentration vs relative MOGAT-2 activity.

All the compounds exemplified herein have an $IC_{50}$ of less than 100 nM, and example 2 exhibits an $IC_{50}$ of 12 nM in this MOGAT-2 in vitro assay.

Inhibitory Activity in MOGAT-2 Cell Assay

The inhibitory activity of compounds against human MOGAT-2 in a cell environment is evaluated in this assay. Caco-2 is a human colon carcinoma cell line and is often used as a model for intestinal epithelial cells. Caco-2 does not express MOGAT-2, and, thus, human MOGAT-2 is engineered into the cell line through a stable transfection. A MAG analogue, 2-O-Hexadecylglycerol (HDG), is utilized to detect cellular MOGAT-2 activity, because HDG is not hydrolyzed and the resulting product is readily monitored by mass spectrometry. The substrate is delivered to cells using as a mixture with DOPC in the form of sonicated vesicles.

Seed the Caco2 cells onto 100 mm dishes to be 80% confluent after 24 hours in complete media (3/1 DMEM: F12+ 10% FBS+20 mM HEPES+gentamicin). Transfect the cells with hMOGAT-2 plasmid (MOGAT-2-pCDNA3.1-Hygro) using Lipofectamine 2000 (Invitrogen). After a 6 hour exposure to the transfection mixture, wash the cells three times in PBS and then add media. Incubate the cells for an additional 18 hours incubation, trypsinize the cells and serially dilute them into 100 mm dishes. Add complete media+400 µg/ml hygromycin and incubate until clones appear. Isolate and transfer the clones into 24 well dishes and grow to confluence. Prepare the RNAs from these clones using a Qiagen RNAeasy kit. Perform Taqman analysis using an ABI inventoried assay (HS00228262) on a 7900 Sequence Detection System (ABI). Analyze the lysates from these clones by Western blot analysis using a goat polyclonal antibody (Santa Cruz, SC-32392 to confirm human MOGAT-2 expression of a 38 kD protein corresponding to MOGAT-2.

Mix 2-O-hexadecylglycerol ("HDG", Biosynth Chemistry & Biology, # H-1806, 562.7 µl of 20 mg/ml) and DOPC (14.3 ml of 20 mg/ml) in chloroform in a glass tube; dry first under $N_2$ gas; and then under reduced pressure for additional 30 minutes. Add 20 ml of buffer (150 mM Tris-Cl pH 7.4, 250 mM sucrose, 1 mM EDTA) to the dried HDG/DOPC mixture while sonicating until the solution becomes clear. Plate the Caco2 cells into a poly-D-lysine coated 96-well plate (the "Cell Plate") at 37° C., 5% $CO_2$ overnight. Remove the growth media and pretreat the cells with the test compound in DMEMF12 (3:1) media (GIBCO 93-0152DK) containing 2% BSA (Sigma) for 30 minutes. Treat the cells with one test compound in 2% BSA DMEMF12 (3:1) media containing 40 µM of oleic acid and 800 µM of 8.9:91.9 (molar ratio) HDG/DOPC for 4 hours. Trypsinize the cells with 50 µl of trypsin solution and add 50 µl of PBS. Immediately freeze the cells on dry ice and store at −20° C. for LC-MS analysis. Extract the cells with chloroform/methanol as follows: transfer the cells to a 2 ml plate; wash the cell plate with 200 µL methanol and then transfer the methanol wash to the 2 ml plate; wash the cell plate again with 200 µL PBS and transfer the PBS wash to the 2 ml plate. Add chloroform (400 µL) with internal standard (19.52 ng/mL) DAG (15:0,15:0 (Sigma)), D5-TAG (39.03 ng/mL) CDN (16,16,16) to the 2 mL Plate. Turn the sealed 2 mL Plate up and down (10×), then vortex and spin. Remove 400 µL of the lower layer from the 2 mL plate and add to the wells of another plate the "Final Plate". Add $CHCl_3$:MeOH (400 µL 2:1) to the 2 mL Plate. Again turn the sealed 2 mL Plate up and down (10×), vortex and spin. Remove 220 µL of the lower layer from the 2 mL Plate and add to the Final Plate. Dry the Final Plate and reconstitute with 500 mL of IPA. Seal the Final Plate and shake for 5 min. Inject 10 µl of a sample from the Final Plate onto a Halo C8 column (2.1×50, 2.7 uL particle size) held at 60° C. using a Leap auto sampler with a 10 µL loop, interfaced to a Shimadzu solvent delivery system. Monitor the channels to collect data for the D5 C16 TAG internal standard as well as the ether TAG, and C52 and C54 natural TAGs. Solvent A is 80/20 $H_2O$/Methanol with 20 µM ammonium acetate. Solvent B is 50/50 IPA/THF with 20 µM ammonium acetate. Flow rate is 0.4 mL/min. Wash solvents were $H_2O$/MeOH and DCM. Using Xcalibur software extract the areas of the peaks of interest, and export the data to Excel which uses the following formula: (area of ether TAG/area of C54 natural TAG)/Area of IS. This ratio effectively accounts for variance of cell number in each well. The results for this MOGAT-2 cell based assay are provided below in Table 3. The results of the MOGAT-2 cell based assay demonstrate that the Examples listed in Table 6 inhibit the human MOGAT-2 in the cell environment.

TABLE 3

| Example | $IC_{50}$ nM (Std Dev., n*) |
| --- | --- |
| 2 | 44 (27, 4) |
| 3 | 274 (261, 17) |
| 5 | 16 (1, 2) |
| 11 | 98 (34, 2) |
| 14 | 40 (21, 3) |
| 16 | 94 (94, 4) |

Pharmacological Effects in a Dog Oil Bolus Model

Inhibiting MOGAT-2 found in the small intestine may be useful for treating hypertriglyceridemia caused by excessive fat intake. To assess the ability of the exemplified compounds to inhibit TAG absorption, twenty one male beagles (n=7 per treatment group) are enrolled for each study, each dog selected to have a body weight between 9-13 kg. House the dogs in cages with a standard light cycle (12 hours light and 12 hours dark); at room temperature: 72±8° F.; and at 30%-70% relative humidity. Fast the dogs for 16 hours prior to the start of the study, then dose the fasted dogs with vehicle (1% HEC, 0.25%, Tween 80, Antifoam) or one of the test compounds in that vehicle. Bleed the dogs one hour after dosing, (0.5 ml from the jugular vein) for a time 0 sample. Dose the dogs with olive oil (Sigma Catalog#: O-1514, 5 ml/kg) immediately after collection of the time 0 sample. Collect samples into an EDTA tube on ice at 1.5, 2, 3, 5, 7, and 9 hrs post compound/vehicle dosing. Centrifuge the samples at 9000 cpm for 15 min and analyze (Roche Cat no. 1877771) for plasma total triglyceride using a Roche Hitachi 917. For plasma TAG 18.1_18.1_18.1 measurement, extract the samples and perform LC/MS/MS analysis similarly to that described above in MOGAT-2 Cell Assay using 10 µL of plasma/.

The analyte is the [M+NH4]+ ion of TAG 18:1 18:1 18:1, which has a mass of 902.8 m/z; the internal standard is D5 TAG 16:0 16:0 16:0, which has a mass of 829.8 m/z. Report the ratio of the 603.5 m/z daughter ion of 902.8 m/z (TAG 18:1 18:1 18:1) and the 556.5 m/z daughter ion of 829.8 m/z (D5 TAG 16:0 16:0 16:0 internal standard) changes in TAG 18:1 18:1 18:1 relative amount. Calculate the net plasma TAG AUC from total TAG AUC minus baseline TAG AUC using Graphpad Prism4: (Net $AUC_{TAG}=AUC_{TAG}$ post oil bolus– $AUC_{TAG}$ at 0 hour). The percent inhibition of plasma triglyceride is calculated as follows: the (oil bolus group mean of net TAG AUC–oil bolus group mean of net TAG AUC with compound treatment/oil bolus group mean of net TAG AUC) *100. The final statistic analysis uses Dunnett's method of One way Anova for comparison with the control. All Net TAG AUC values are transformed to ranked averaged AUC for comparison to limit the variability within the studies. The ability of exemplified compounds of the present invention to inhibit MOGAT-2 activity and reduce TAG absorption in vivo can be further evaluated according to this assay.

Example 2 was evaluated in this model in three studies at 30 mg/kg dose and in two studies at the 75 mg/kg dose. Combination of results from those studies demonstrated statistically significant (p<0.05) reduction in excursion of postprandial triglycerides. Results were as follows: 43% inhibition of TAG absorption (45% of 18.1 TAG) at 30 mg/kg PO and 64% inhibition of TAG absorption (63% of 18.1 TAG) at 75 mg/kg PO.

The exemplified compound of the present invention can be readily formulated into pharmaceutical compositions in accordance within accepted practices such as found in Remington's Pharmaceutical Sciences, Gennaro, Ed., Mack Publishing Co. Easton Pa. 1990. A treating physician or other medical person will be able to determine an effective amount of the compound for treatment of a person in need, particularly for the treatment of hypertriglyceridemia. Preferred pharmaceutical compositions can be formulated as a tablet or capsule for oral administration. The tablet or capsule can include a compound of the present invention in an effective amount for treating a patient in need of treatment.

What is claimed is:

1. A compound of the formula below:

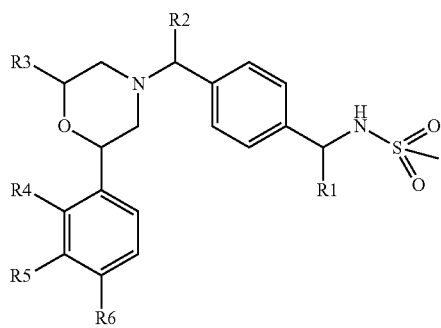

wherein
R1 is selected from: —CH$_3$ and —CF$_3$;
R2 is selected from: H and —CH$_3$;
R3 is selected from: H and —CH$_3$;
R4 is selected from: H, —OC$_{1-3}$alkyl, and halogen;
R5 is selected from: H, —CF$_3$, —OCH$_3$, and halogen;
R6 is selected from: H and halogen;
provided that at least one of R4, R5, and R6 is H;
or a pharmaceutically acceptable salt thereof.

2. A compound according to claim 1 wherein R1 is —CH$_3$.
3. A compound according to claim 1 wherein R1 is —CF$_3$.
4. A compound according to claim 1 wherein R2 is H.
5. A compound according to claim 1, wherein R3 is H.
6. A compound according to claim 1 wherein R4 is selected from H and halogen.
7. A compound according to claim 1 wherein R5 is selected from: H, —CF$_3$, F, and Cl.
8. A compound according to claim 1 wherein R5 is H.
9. A compound according to claim 1 where R6 is F.
10. A compound of the formula below:

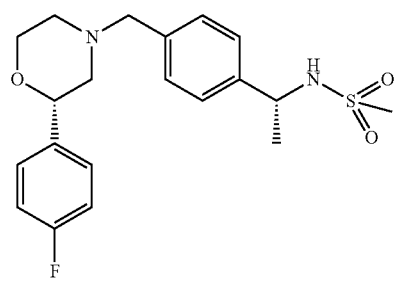 [SMILES: C[C@@H](NS(C)(=O)=O)c1ccc(CN2CCO[C@@H](c3ccc(F)cc3)C2)cc1]

or a pharmaceutically acceptable salt thereof.

11. A compound of according to claim 1 wherein the pharmaceutically acceptable salt is selected from: a chloride salt and a maleate salt.

12. A compound of according to claim 11 wherein the pharmaceutically acceptable salt is a maleate salt.

13. A compound which is N-[(1R)-1-(4-{2S)-2-(4-Fluorophenyl)morpholin-4-yl]methyl}phenyl)ethyl]methanesulfonamide hydrochloride.

14. A compound which is N-[1R)-1-(4-{[(2S)-2-(4-Fluorophenyl)morpholin-4-yl]methyl}phenyl)ethyl]methanesulfonamide maleic acid.

15. A pharmaceutical composition comprising a compound according to claim 1 and at least one of a pharmaceutically acceptable carrier, diluent, or excipient.

16. A method of treating a patient in need of treatment for hypertriglyceridemia, the method comprises administering to the patient an effective amount of a compound, according to claim 1.

17. A method of treating a patient in need of treatment for hypertriglyceridemia, the method comprises administering to the patient an effective amount of a compound, according to claim 10.

18. A pharmaceutical composition comprising a compound according to claim 10 and at least one of a pharmaceutically acceptable carrier, diluent, or excipient.

* * * * *